Figure 1:
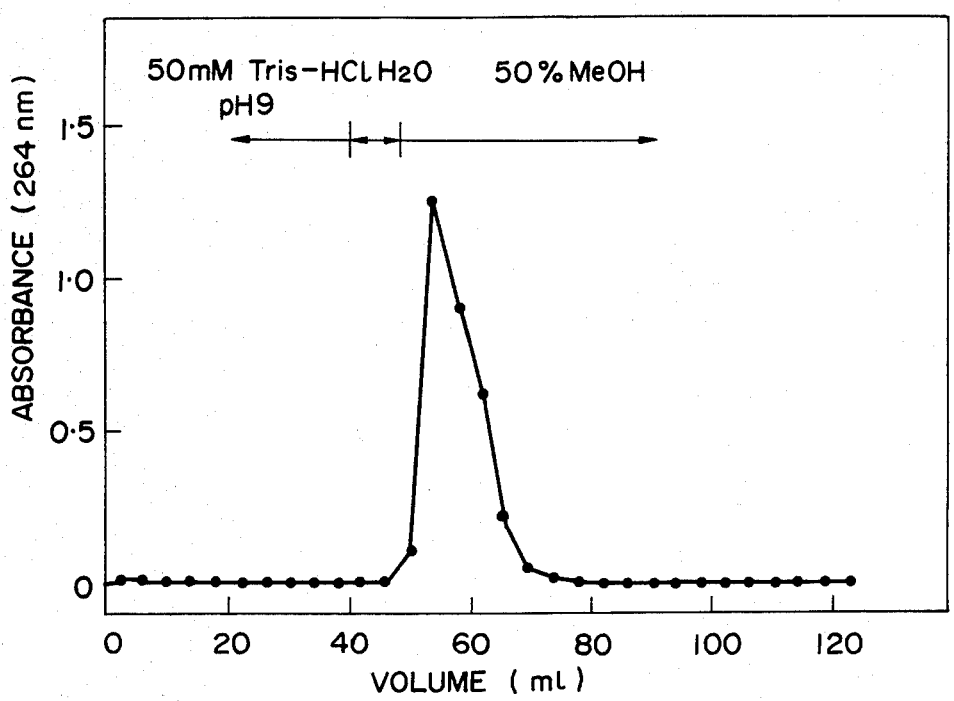

United States Patent [19]

Hayatsu et al.

[11] Patent Number: 4,490,525

[45] Date of Patent: Dec. 25, 1984

[54] POLYSACCHARIDES CONTAINING PHTHALOCYANINE NUCLEUS

[75] Inventors: Hikoya Hayatsu, Okayama; Yasuo Tezuka, Nara, both of Japan

[73] Assignee: Sumitomo Chemical Company, Limited, Osaka, Japan

[21] Appl. No.: 394,441

[22] Filed: Jul. 1, 1982

[51] Int. Cl.³ .................. C07B 37/00; C07B 37/16
[52] U.S. Cl. .................... 536/54; 536/18.1; 536/46; 536/55.1; 536/121; 536/1.1
[58] Field of Search ............ 536/1, 17.5, 18.1, 45, 536/46, 121, 54, 55.1

[56] References Cited

PUBLICATIONS

Arimoto et al., Cancer Letters, 11 (1980), 29-33.
Arimoto et al., Biochemical and Biophysical Research Communications, vol. 92, No. 2, 1980 (pp. 662-668).

Primary Examiner—Johnnie R. Brown
Assistant Examiner—Elli Peselev
Attorney, Agent, or Firm—Cushman, Darby & Cushman

[57] ABSTRACT

Metal-containing or metal-free phthalocyanine-polysaccharide complex defined below is used for removal of mutagens and carcinogens present in aqueous solutions, the said complex having formula of

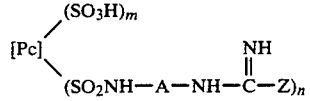

wherein Pc is a metal-containing or metal-free phthalocyanine residue, A is an alkylene group having 2 to 6 carbon atoms or an arylene group having 1 to 3 rings, the integers m and n satisfy both $2 < m+n \leq 4$ and $1 \leq n \leq 2$, and Z is an activated polysaccharide residue.

13 Claims, 3 Drawing Figures

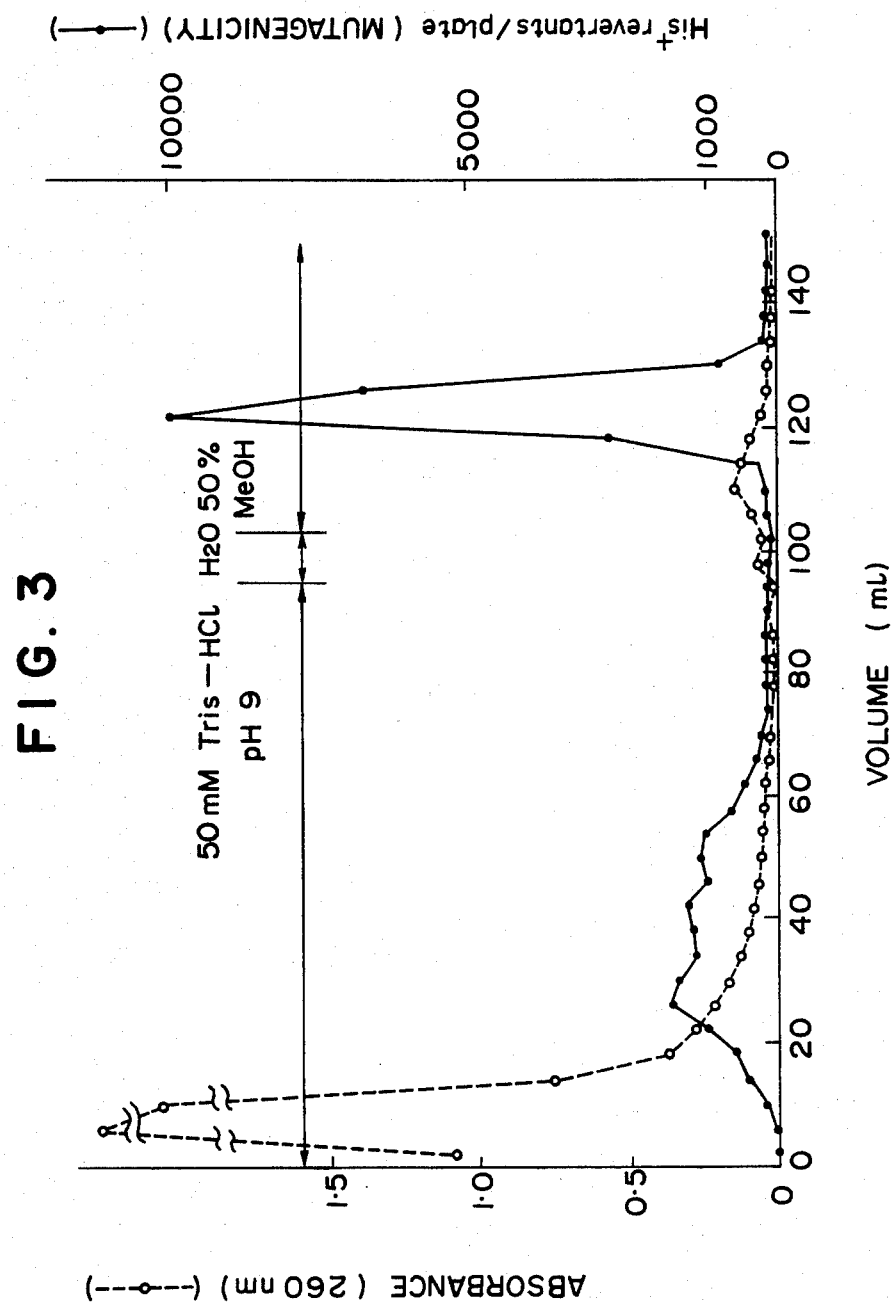

POLYSACCHARIDES CONTAINING PHTHALOCYANINE NUCLEUS

The present invention relates to metal-containing or metal-free phthalocyanine-polysaccharide complexes, or polysaccharide derivatives having phthalocyanine nucleus, which are useful for removal, through selective adsorption, of mutagens and carcinogens present in a solution, particularly in an aqueous solution, in a minute amount.

In recent years, effects, against human, of hazardous materials, particularly mutagens and carcinogens, present in the environment, food stuffs, etc. have come to public notice. Accordingly, development of technologies to detect and to remove such substances has been an important issue in addition to studies on the effects of these substances against human.

An object of the present invention is to provide a novel agent useful for removal, through selective adsorption, of mutagens and carcinogens present in a solution, particularly in an aqueous solution, in a minute amount.

For example, ligand-polysaccharides obtained by coupling a ligand, such as a substrate analog for enzyme, with an activated polysaccharide which is prepared by activating a gel-formable polysaccharide with an activating agent, for example, with cyanogen bromide, have so far been utilized for fractionation or purification of specific enzyme molecules. The present inventors have investigated various ligands that can bind to mutagens, and have reached the present invention.

The present invention is to provide phthalocyanine-polysaccharide complexes represented by the general formula (I), when they are shown as the free acid,

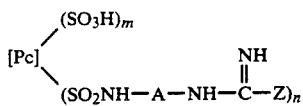

(wherein Pc is a metal-containing or metal-free phthalocyanine residue; A is an alkylene group having 2 to 6 carbon atoms or an arylene group having 1 to 3 rings; m and n are integers satisfying both the $2 < m+n \leq 4$ and $1 \leq n \leq 2$ equations; and Z is an activated polysaccharide residue). The present invention also provides a process for preparing the complexes above and a method for treating mutagens and carcinogens using the prepared materials.

In the accompanying drawings:

FIG. 1 shows adsorption and elution of Trp-P-1,[1] a mutagenic carcinogen, through a column of copper phthalocyanine-polysaccharide
[1] Abbreviations; Trp-P-1, 3-amino-1,4-dimethyl-5H-pyrido[4,3-b]-indole; Trp-P-2, 3-amino-1-methyl-5H-pyrido[4,3-b]-indole.

Figure 2:
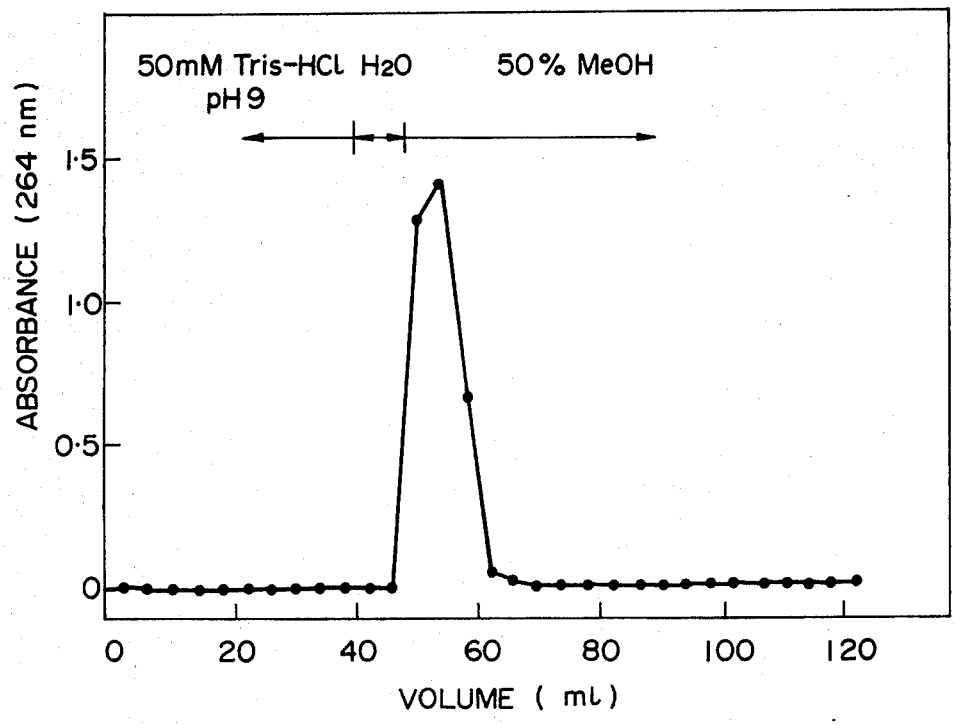

FIG. 2 those of Trp-P-2; and

FIG. 3 those of mutagens formed by pyrolysis of tryptophan.

The phthalocyanine-polysaccharide complexes of the present invention are obtained by coupling activated polysaccharide with a water-soluble compound, as the ligand, represented by the general formula (II), when it is shown as the free acid,

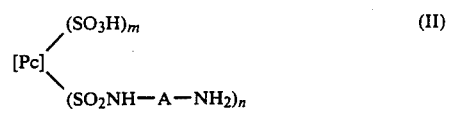

(wherein Pc is a metal-containing or metal-free phthalocyanine residue; A is an alkylene group having 2 to 6 carbon atoms or an arylene group having 1 to 3 rings; and integers m and n are those satisfying both the $2 < m+n \leq 4$ and $1 \leq n \leq 2$ equations).

The metal contained in the phthalocyanine nucleus of the water-soluble compound represented in the general formula (I) of the present invention, if it is present, is, for example, copper, iron, nickel, cobalt and aluminum. The alkylene group can be straight-chained or branched alkylene groups having 2 to 6 carbon atoms. The arylene group is phenylene, biphenylene, terphenylene and other groups having 1 to 3 rings.

The polysaccharide to be activated and employed in the coupling according to the present invention can be agarose, dextrin and the like.

The process for the preparation of the phthalocyanine-polysaccharides according to the present invention will be more fully described below. For instance, copper phthalocyanine is allowed to react with chlorosulfonic acid at a temperature of 130° to 135° C., and the reaction mixture is poured into ice water. Crystals that precipitate are collected by filtration and washed with ice water, to obtain a wet cake of chlorosulfonyl-sulfo-copper-phthalocyanine compound. The wet cake is added to cold water of which temperature is 0° to 5° C. After neutralization of the mixture with an alkali solution to pH 5, the temperature is raised to 15° C. To the mixture is added a diamine represented by the formula: $H_2N-A-NH_2$ (wherein A is as defined above) (1 to 1.5 moles based on the phthalocyanine) in one portion, and the resulting mixture is adjusted to pH 9 to 11 by addition of an alkali solution and is kept at a temperature of 20° to 25° C. Thus, a ligand solution of the structure represented by the general formula (II) is obtained.

On the other side, a polysaccharide derivative is reacted with cyanogen bromide in a potassium phosphate buffer solution (pH 11.9), thereby to prepare a cyanogen bromide-activated polysaccharide, which is then mixed with the above-mentioned ligand solution. The mixture is shaken overnight for the coupling. A primary amine is then added to the mixture to block the excess active group, and the resulting phthalocyanine-polysaccharide complex is well washed with an acetate buffer and a sodium bicarbonate buffer successively.

The phthalocyanine-polysaccharide complexes of the present invention are capable of removing mutagens and carcinogens, especially the polycyclic ones, from their dilute solutions, particularly from their aqueous solutions by selective adsorption. A mutagen in the present invention is a substance which can induce inheritable genetic change in organisms. According to the present invention, further, mutagens and carcinogens may be efficiently concentrated through the adsorption and desorption.

A more detailed description of the present invention follows, in which the "parts" represent weight.

EXAMPLE

(1) Preparation of [N-(6-aminohexyl)sulfamoyl]-polysulfophthalocyanatocopper (II)

Into 184 parts by weight of chlorosulfonic acid was added 23.7 parts of copper-phthalocyanine at a temperature of 20° to 25° C. under stirring. Then, the temperature of the mixture was raised to 130° C. during 1 hour and the mixture was kept at 130° to 135° C. for 10 hours under stirring. After completion of the reaction, the mixture was allowed to cool down to 50° C. and poured slowly into a mixture of 170 parts of water, 770 parts of ice blocks and 43 parts of sodium chloride during a period of about 30 minutes. Thereafter, the mixture was suction-filtered and the filter cake was washed three times with 200 parts in total of cold water cooled to 5° C. The resulting wet cake was suspended in a mixture of 200 parts of water and 100 parts of ice, and the suspension was neutralized with an aqueous 15% soda ash solution to pH 5. The temperature of the suspension was slowly raised to 15° C. while the pH was maintained at 4 to 5. The pH was then adjusted to 8 by addition of an aqueous 15% soda ash solution. Into the mixture was added 60 parts of an aqueous 10% hexamethylenediamine in one portion. The temperature of the mixture was raised to 20° C., and the mixture was stirred for 6 hours while the temperature was kept at 20° to 25° C. and the pH at 10 to 10.5. The reaction mixture was allowed to concentrate to dryness by keeping it 80° C. for 40 hours, to leave 48 parts of a blue pigment mainly composed of [N-(6-aminohexyl)sulfamoyl]-polysulfophthalocyaninatocopper (II). The pigment was found to have 0.54 [N-(6-aminohexylsulfamoyl] group per phthalocyanine nucleus by determination with high performance liquid chromatography. Though the material contains, besides the main component, pigments such as polysulfophthalocyaninatocopper (II) and N,N'-hexamethylene-bis(sulfamoyl-polysulfophthalocyaninatocopper (II)) as impurity, they can be removed by the washing as described in the following item (4).

(2) Preparation of cyanogen bromide-activated agarose gel

Sixty parts of agarose (Sepharose 4B manufactured by Pharmacia Co.) was washed with water, and then with 200 parts of a 0.5M potassium phosphate buffer (pH 11.9). A solution of 4.2 parts of cyanogen bromide in 120 parts of the 0.5M potassium phosphate buffer was prepared under cooling at 0° to 5° C. The solution was slowly added to the washed Sepharose 4B mentioned above, and the mixture was shaken for about 8 minutes at a temperature of 5° C. to complete the reaction. The resulting cyanogen bromide-activated agarose gel was washed well with water and then washed quickly with 0.1M sodium bicarbonate buffer (pH 8.3) containing sodium chloride in an amount corresponding to 0.5M concentration (hereafter referred to as the coupling buffer).

(3) Preparation of a ligand solution

Three parts of the [N-(6-aminohexyl)sulfamoyl]-polysulfophthalocyaninatocopper (II) pigment as prepared in item (1) were dissolved in 120 parts of the coupling buffer. A small amount of insoluble matter that precipitated was removed by filtration.

(4) Preparation of the phthalocyanine-polysaccharide complex

The ligand solution as prepared in the item (3) was added into the cyanogen bromide-activated agarose gel as prepared in the item (2), and the mixture was shaken for 15 hours at room temperature. After the unreacted ligand was removed by washing with the coupling buffer, the gel was mixed with 120 parts of an aqueous 1M monoethanolamine solution, and the mixture was shaken for 4 hours at room temperature. The mixture was transferred to a column and the gel was washed first with 1000 parts of an aqueous 8M urea solution, secondly with 1000 parts of an aqueous 3.8M potassium chloride solution, and finally with a sufficient amount of water, to leave a gel of [N-(6-aminohexyl)sulfamoyl]-polysulfophthalocyaninatocopper (II)-agarose complex.

(5) Determination of copper in the phthalocyanine-polysaccharide complex

Ligand content in the gel was estimated by determining copper in the material.

Ten milliliters of the phthalocyanine-polysaccharide complex was dried and weighed (255 mg). Each 20 mg of the dried sample was placed in 5 crucibles and treated at a temperature of 500° for 10 hours for incineration. Each of ashes thus obtained was dissolved in 5 ml of 6N hydrochloric acid and diluted with water to 25 ml to make a sample solution.

The sample solution was determined by measuring the atomic absorption. Calculation based on a calibration curve obtained for standard copper sulfate solutions showed that one ml of the phthalocyanine-polysaccharide gel contained 296 nmole of copper atom.

Sepharose 4B itself was analyzed in the same way and was found to contain no copper.

(6) Isolation of mutagens by affinity chromatography

A chromatographic column of the gel of [N-(6-aminohexyl)sulfamoyl]-polysulfophthalocyaninatocopper(II)-agaraose complex (item 4) was prepared (0.7×5.5 cm, 2.1 ml), and was equilibrated with 50 mM Tris-HCl buffer, pH 9.

(i) A solution of 300 nmole of Trp-P-1 (a carcinogenic mutagen formed on pyrolysis of tryptophan) (12.6 $A_{264}$ units) in 1 ml of 50 mM Tris-HCl solution (pH 9) was passed through the column. The column was eluted sequentially with the same buffer solution, water and 50% methanol, and the fractions were monitored for the amount of Trp-P-1 by the absorbance at 264 nm. The pattern of elution of Trp-P-1 is shown in FIG. 1, which shows that Trp-P-1 is not eluted by the 50 mM Tris-HCl buffer, but by 50% methanol. The recovery was 98%.

Similarly, 280 nmole of Trp-P-2 (another carcinogenic mutagen formed on pyrolysis of tryptophan) (14 $A_{264}$ units) was loaded on the column and eluted. As FIG. 2 shows, Trp-P-2 was eluted with 50% methanol. The recovery was 97%.

(ii) Next, the tarry substance formed on pyrolysis of of tryptophan was subjected to the chromatography. Five hundred milligrams of tryptophan was heated for 4 minutes in a casserole which was placed above a flame. From the resulting tarry substance, dichloromethane-soluble basic fraction was obtained. This material dissolved in 50 mM Tris-HCl buffer (pH 9) was applied to the column, and the column was eluted in the way described for Trp-P-1. Fractions were monitored for their mutagenicity and the absorbance at 260 nm. The mutagenicity was measured by the standard Salmonella/mammalian microsome test of Ames [as modified by Yahagi et al., Mutation Research, 48, 121–130 (1977)]. As FIG. 3 shows, most of the ultraviolet-absorbing material, that was non-mutagenic, was eluted in the first several fractions, and the major mutagenic components were eluted only after the solvent was changed to 50% methanol.

We claim:

1. A phthalocyanine-polysaccharide complex represented by the formula, when it is shown as a free acid,

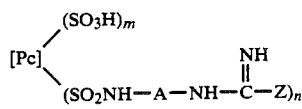

wherein Pc is a copper, iron, nickel, cobalt or aluminum containing or metal-free phthalocyanine residue; A is an alkylene group having 2 to 6 carbon atoms or an arylene group having 1 to 3 rings; m and n are integers satisfying both the $2 < m+n \leq 4$ and $1 \leq n \leq 2$ equations; and Z is an activated polysaccharide residue selected from the group consisting of agarose and dextrin.

2. A phthalocyanine-polysaccharide complex according to claim 1, which has the formula, when it is shown in the free acid,

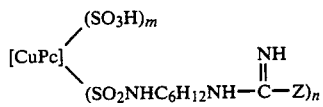

wherein CuPc is copper phthalocyanine residue and Z, m and n are the same as defined in claim 1.

3. A process for preparing a phthalocyanine-polysaccharide complex formula, when it is shown in the free acid,

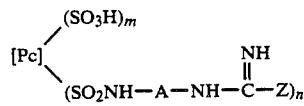

wherein Pc is a copper, iron, nickel, cobalt or aluminum containing or metal-free phthalocyanine residue; A is an alkylene group having 2 to 6 carbon atoms or an arylene group having 1 to 3 rings; m and n are integers satisfying both the $2 < M+n \leq 4$ and $1 \leq n \leq 2$ equations; and Z is an activated polysaccharide residue selected from the group consisting of agarose and dextrin which comprises coupling activated polysaccharide with a water-soluble compound, as the ligand, represented by the general formula, when it is shown as the free acid,

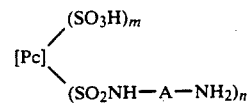

4. A method for removal of mutagens from aqueous solution, comprising adsorbing the mutagen in aqueous solution by using a phthalocyanine-polysaccharide complex represented by the formula, when it is shown as the free acid,

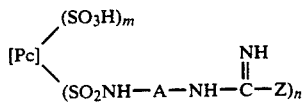

wherein Pc is a copper, iron, nickel, cobalt or aluminum containing or metal-free phthalocyanine residue; A is an alkylene group having 2 to 6 carbon atoms or an arylene group having 1 to 3 rings; m and n are integers satisfying both the $2 < m+n \leq 4$ and $1 \leq n \leq 2$ equations; and Z is an activated polysaccharide residue selected from the group consisting of agarose and dextrin.

5. A phthalocyanine-polysaccharide complex according to claim 1 wherein the activated polysaccharide residue is a residue of agarose.

6. A phthalocyanine-polysaccharide complex according to claim 2 wherein the activated polysaccharide residue is a residue of agarose.

7. A method according to claim 4 wherein the activated polysaccharide residue is a residue of agarose.

8. A phthalocyanine-polysaccharide complex according to claim 1 wherein the activation had been carried out with cyanogen bromide.

9. A phthalocyanene-polysaccharide complex according to claim 2 wherein the activation had been carried out with cyanogen bromide.

10. A process according to claim 3 wherein the activation had been carried out with cyanogen chloride.

11. A method according to claim 4 wherein the activation had been carried out with cyanogen bromide.

12. A method according to claim 4 including the additional step of eluting the mutagen.

13. A method according to claim 12 wherein the activation had been carried out with cyanogen bromide.

* * * * *